(12) United States Patent
Jain et al.

(10) Patent No.: US 10,239,816 B2
(45) Date of Patent: Mar. 26, 2019

(54) PROCESS FOR PRODUCING (METH)ACRYLIC ACID

(71) Applicant: Arkema France, Colombes (FR)

(72) Inventors: Sandeep Jain, Paris (FR); Christian Lacroix, Forbach (FR); Michel Jean Fauconet, Valmont (FR)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 15/556,308

(22) PCT Filed: Mar. 4, 2016

(86) PCT No.: PCT/FR2016/050501
§ 371 (c)(1),
(2) Date: Sep. 7, 2017

(87) PCT Pub. No.: WO2016/142608
PCT Pub. Date: Sep. 15, 2016

(65) Prior Publication Data
US 2018/0079706 A1    Mar. 22, 2018

(30) Foreign Application Priority Data

Mar. 12, 2015 (FR) ..................... 15 52049

(51) Int. Cl.
*B01D 3/10* (2006.01)
*B01D 5/00* (2006.01)
*C07C 51/25* (2006.01)
*C07C 51/44* (2006.01)
*C07C 57/04* (2006.01)

(52) U.S. Cl.
CPC ............. *C07C 51/44* (2013.01); *B01D 3/10* (2013.01); *B01D 5/0045* (2013.01); *C07C 51/252* (2013.01)

(58) Field of Classification Search
CPC ......... C07C 51/44; C07C 51/252; B01D 3/10; B01D 5/0045
See application file for complete search history.

(56) References Cited

U.S. PATENT DOCUMENTS

| 5,921,755 | A | * | 7/1999 | Eldridge | ............... F04B 37/14 417/255 |
|---|---|---|---|---|---|
| 6,677,482 | B2 | | 1/2004 | Nishimura et al. | |
| 7,151,194 | B2 | | 12/2006 | Ueno et al. | |
| 7,288,169 | B2 | | 10/2007 | Yada et al. | |
| 8,242,308 | B2 | * | 8/2012 | Ho | ..................... C07C 51/44 562/600 |
| 2005/0260085 | A1 | | 11/2005 | Conrad et al. | |

FOREIGN PATENT DOCUMENTS

| EP | 2 066 613 B1 | 6/2012 |
|---|---|---|
| JP | 2007231935 * | 9/2007 |
| WO | WO 2008/033687 A2 | 3/2008 |

OTHER PUBLICATIONS

English Translation of JP2007231935, dated Sep. 13, 2007, pp. 1-20. (Year: 2007).*
Yu et al., "Propylene from Renewable Resources: Catalytic Conversion of Glycerol into Propylene," ChemSusChem, 2014, 7, 743-747 (Year: 2014).*

* cited by examiner

Primary Examiner — Pancham Bakshi
Assistant Examiner — Mark R Luderer
(74) Attorney, Agent, or Firm — Lynn B. Morreale

(57) ABSTRACT

The invention is directed to a process for recovering/purifying (meth)acrylic acid which does not use azeotropic solvent and is based on the use of two columns for purifying a reaction mixture comprising (meth)acrylic acid. The process according to the invention includes a dry vacuum pump condensation system, which makes it possible to reduce the amount of final aqueous discharges.

12 Claims, 2 Drawing Sheets

PROCESS FOR PRODUCING (METH)ACRYLIC ACID

CROSS-REFERENCE TO RELATED APPLICATIONS

This application is a national stage application under 35 U.S.C. § 371 of PCT/FR2016/050501, filed Mar. 4, 2016 which claims benefit to application FR15.52049, filed Mar. 12, 2015.

TECHNICAL FIELD

The present invention relates to the production of (meth) acrylic acid.

One subject of the invention is more particularly a process for recovering/purifying (meth)acrylic acid which does not use azeotropic solvent and is based on the use of two columns for purifying a reaction mixture comprising (meth) acrylic acid. The process according to the invention includes a dry vacuum pump condensation system, which makes it possible to reduce the amount of final aqueous discharges.

The invention also relates to a plant suitable for the implementation of this process.

TECHNICAL BACKGROUND AND TECHNICAL PROBLEM

Manufacturers have been developing processes for synthesizing acrylic acid for decades.

The process which today is the most widely exploited industrially uses a catalytic oxidation reaction of propylene in the presence of oxygen.

This reaction is generally conducted in the gas phase, and most often in two steps: the first step carries out the substantially quantitative oxidation of propylene to give an acrolein-rich mixture, then, during the second step, the selective oxidation of acrolein to give acrylic acid is carried out.

The reaction conditions of these two steps, carried out in two reactors in series or in a single reactor containing the two reaction steps in series, are different and require catalysts suitable for the reaction; it is not however necessary to isolate the intermediate acrolein during this two-step process.

The gas mixture resulting from the second step consists, apart from acrylic acid:

- of impurities resulting from the first reaction step which have not reacted;
- of light compounds that are noncondensable under the temperature and pressure conditions customarily used, unconverted in the first step or formed in the second step: nitrogen, unconverted oxygen, carbon monoxide and dioxide formed in a small amount by final oxidation or going round and round, by recycling, in the process;
- of condensable light compounds unconverted in the first step or formed in the second step: water, unconverted acrolein, light aldehydes such as formaldehyde and acetaldehyde, formic acid, acetic acid or propionic acid;
- of heavy compounds: furfuraldehyde, benzaldehyde, maleic acid and anhydride, benzoic acid, 2-butenoic acid, phenol, protoanemonin.

The complexity of the gas mixture obtained in this process makes it necessary to carry out a set of operations for recovering the acrylic acid contained in this gaseous effluent and convert it to a grade of acrylic acid that is compatible with the final use thereof, for example the production of acrylic acid polymers, or the production of acrylic ester polymers.

The first step of this recovery/purification phase consists of an extraction of the acrylic acid by countercurrent absorption in a solvent, generally water supplied by an external source and/or originating from the process. The amounts of water and of gaseous reaction mixture are such that the weight content of acrylic acid in the crude aqueous solution produced is generally of the order of 40% to 80%.

Nevertheless, a very significant economic problem is faced, mainly due to the expensive energy needed for eliminating the water used as acrylic acid absorption solvent, in so far as the effective elimination of the water without excessive loss of (meth)acrylic acid is complicated by the existence of interactions (hydrogen bonds) between the two compounds.

Thus, this separation operation is generally carried out on the industrial scale by distillation with a third azeotropic solvent, which contributes to increasing the number of distillation columns and their associated energy costs. Moreover, the increase in the number of distillation columns leads to an additional cost linked to the supplementary consumption of polymerization inhibitors that must be introduced into each of said columns in order to purify the desired product and eliminate the by-products while preventing the problems of fouling of the equipment by polymerization of the monomer.

One alternative to this process that uses water as acrylic acid absorption solvent is to use a hydrophobic heavy solvent to extract the acrylic acid, but such a process does not simplify the acrylic acid purification process.

Recently, in order to overcome these various drawbacks, new "solvent-free" technologies for recovering/purifying acrylic acid have appeared, involving a reduced number of purification steps and eliminating the introduction of external organic solvent.

In the acrylic acid production process described in U.S. Pat. No. 7,151,194, the gaseous reaction mixture is sent to an absorption column and brought into contact with an aqueous absorption solution, in order to obtain an aqueous solution of acrylic acid, which is then distilled in the absence of azeotropic solvent. A stream of crude acrylic acid is obtained as bottoms or as a sidestream from the distillation column, which is then sent to a unit for purification by crystallization. One drawback of this process is that the introduction of external water as absorption solvent makes it difficult to eliminate the water at the top of the absorption column without a significant loss of acrylic acid, and to recover a quality of crude acrylic acid having a low concentration of water as a sidestream, when this process is carried out in a two-column configuration.

Patent EP 2 066 613 describes a process for recovering acrylic acid without using external water, or azeotropic solvent and that only uses two columns for purifying the cooled gaseous reaction mixture: a) a dehydration column, b) and a finishing column (or purification column) fed by a portion of the bottom stream from the dehydration column.

The dehydration column generally operates at atmospheric pressure or slightly above atmospheric pressure.

In the dehydration column, the gaseous stream distilled as an overhead stream is condensed and sent back in part to the dehydration column in the form of reflux in order to absorb the acrylic acid.

The finishing column generally operates at a pressure below atmospheric pressure, which makes it possible to operate at relatively low temperatures, in order to thus prevent the polymerization of the unsaturated products present, and to minimize the formation of heavy by-products.

In the finishing column, the overhead distillate comprising water and light by-products is condensed then recycled to the bottom of the first column, and a stream comprising acrylic acid enriched in heavy by-products is eliminated as bottoms in order to be used possibly for the production of acrylic esters.

A stream of purified acrylic acid corresponding to a technical grade is recovered by drawing off as a sidestream in liquid or vapour form. The technical acrylic acid obtained generally has a purity of greater than 98.5 wt % and contains less than 0.5 wt % of water.

In this process, a portion of the streams (from the bottom of the dehydration column or from the top of the finishing column) is advantageously sent back to the heating/reboiler devices of the dehydration column and/or used for cooling the gaseous reaction mixture, which makes it possible to optimize the energy requirements of the process. Despite the advantages that the process described in document EP 2 066 613 provides, there still remain drawbacks linked to the implementation thereof.

In particular, at the top of the finishing column which functions under vacuum, the condenser releases residual vapours comprising organic impurities that must be eliminated, for example by incineration, which is harmful for the environment.

There are many vacuum-generating systems available for reducing the operating pressure of the distillation columns (see for example Techniques de l'Ingénieur, Pompes à vide [Vacuum pumps], B4030, Oct. 11, 1983). Generally a distinction is made between "volumetric" pumps which generate the vacuum by using liquid seals (oils, organic products or water), such as for example vane pumps and liquid ring pumps, and "drive" pumps, in which it is the flow of a fluid that creates the vacuum (ejector pumps, steam jet pumps, etc.). The systems most commonly used involve water or steam jet ejectors or liquid ring pumps, mainly water ring pumps.

These systems are not suitable for reducing the operating pressure of the finishing column of a solvent-free (meth) acrylic acid purification process, such as that described in document EP 2 066 613.

Such systems, for example described in document U.S. Pat. No. 6,677,482 or 7,288,169, use steam and generate a large amount of aqueous effluents containing acrylic acid and organic impurities, which cannot be economically recycled to the purification loop formed by the dehydration column and the finishing column. Indeed, it has been observed that the recycling of too large an amount of water at the dehydration column leads to sizeable losses of acrylic acid at the top of this column, unless an oversized column is used but this leads to an expensive investment. These aqueous effluents therefore need to be sent to a water treatment plant or directly to a thermal oxidizer, thus giving rise on the one hand to a loss of high quality product and on the other hand to an environmentally harmful discharge. The effluents from these vacuum systems, rich in noncondensable compounds which are incinerated or sent directly to the atmosphere, release in the first case oxidation products and in the second case organic compounds that are environmental pollutants.

Therefore, there remains a need to eliminate and/or reduce the generation of aqueous discharges in a solvent-free recovery/purification process enabling the finishing column to operate under vacuum.

The inventors have now discovered that the use of a dry vacuum pump linked to the operation of the finishing column in a solvent-free acrylic acid recovery/purification process makes it possible to meet this need, with the economic and environmental advantages that result therefrom.

It has become apparent to the inventors that this invention could be applied to acrylic acid produced from sources other than propylene, to methacrylic acid and also to these acids derived from renewable raw materials, which are capable of posing the same purification problems.

SUMMARY OF THE INVENTION

The present invention relates firstly to a process for recovering (meth)acrylic acid without using azeotropic solvent, starting from a gaseous reaction mixture comprising (meth)acrylic acid obtained by gas-phase oxidation of a precursor of the (meth)acrylic acid, comprising at least the following steps:

i) the gaseous reaction mixture is subjected to dehydration without using azeotropic solvent in a first column, referred to as dehydration column, resulting in an overhead stream, at least a portion of which is condensed and sent back to the dehydration column in the form of reflux, and in a bottom stream;

ii) the dehydration column bottom stream is subjected, at least in part, to a distillation at a pressure below atmospheric pressure in a second column, referred to as finishing column, resulting in an overhead stream and in a bottom stream containing heavy compounds;

iii) a (meth)acrylic acid stream is recovered by drawing off as a sidestream from the finishing column, and/or as bottoms from the finishing column;
said process being characterized in that the overhead stream from the finishing column is subjected, at least in part, to a dry vacuum pump condensation system, forming a condensate that is sent back to the dehydration column, and a final gaseous effluent.

In the present invention, the term "(meth)acrylic" means "acrylic" or "methacrylic".

The term "azeotropic solvent" denotes any organic solvent exhibiting the property of forming an azeotropic mixture with water.

The term "light" describing the by-product compounds denotes the compounds for which the boiling point is lower than that of the (meth)acrylic acid and, analogously, the term "heavy" denotes the compounds for which the boiling point is greater than that of the (meth)acrylic acid.

The process according to the invention may additionally comprise other steps that aim to continue the purification of the (meth)acrylic acid stream recovered in step iii).

According to certain specific embodiments, the invention also exhibits one or preferably several of the advantageous characteristics listed below:

the dry vacuum pump condensation system comprises at least one condenser and one dry vacuum pump (which may also be referred to as primary dry vacuum pump);

the dry vacuum pump condensation system may optionally comprise, in addition to the primary dry vacuum pump, a liquid separator, one or more flame traps, one or more filters, sealing and insulating systems, a dry booster pump or a combination of dry booster pumps, such as for example "Roots"-type pumps (volumetric pumps using two synchronized rotors rotating in opposite directions);

at least one portion of the (meth)acrylic acid stream drawn off as a sidestream is subjected to a dry vacuum pump condensation system, identical to or different from that used for the overhead stream from the finishing column.

According to one embodiment of the invention, the precursor of the (meth)acrylic acid is acrolein.

According to one embodiment of the invention, the acrolein is obtained by oxidation of propylene or by oxydehydrogenation of propane.

According to one embodiment of the invention, the precursor of the (meth)acrylic acid is methacrolein.

According to one embodiment of the invention, the methacrolein is obtained by oxidation of isobutylene and/or of tert-butanol.

According to one embodiment of the invention, the methacrolein is obtained from oxydehydrogenation of butane and/or isobutane.

According to one embodiment of the invention, the gaseous reaction mixture comprising (meth)acrylic acid obtained by gas-phase oxidation of a precursor of the (meth)acrylic acid comprises carbon of renewable origin.

According to one embodiment of the invention, the precursor of the (meth)acrylic acid is derived from glycerol, 3-hydroxypropionic acid or 2-hydroxypropanoic acid (lactic acid).

According to a preferred embodiment of the invention, the gaseous reaction mixture comprises acrylic acid derived from propylene obtained according to a two-step oxidation process.

The process according to the invention produces a stream of (meth)acrylic acid without producing aqueous discharges, and does not require the use of an azeotropic solvent in order to eliminate the water from the process. The process according to the invention also contributes to limiting the losses of (meth)acrylic acid at the top of the dehydration column.

Another subject of the present invention is a plant for recovering (meth)acrylic acid, suitable for implementing the process according to the invention.

The plant according to the invention comprises at least:
a) one dehydration column;
b) one finishing column fluidically connected to the bottom of said dehydration column;
c) at least one dry vacuum pump condensation system fluidically connected to the top of said finishing column;
d) optionally one E230/300 dry vacuum pump condensation system fluidically connected laterally to said finishing column.

It is desired, by "fluidic connection" or "fluidically connected", to indicate that there is connection by a system of pipes capable of transporting a stream of material. This connection system may comprise valves, bypasses, heat exchangers or compressors.

According to certain specific embodiments, the invention also exhibits one or preferably several of the advantageous characteristics listed below:
the dry vacuum pump condensation system comprises at least one condenser fluidically connected to a dry vacuum pump;
the dry vacuum pump condensation system comprises several condensers;
the dry vacuum pump condensation system may optionally comprise a liquid separator, one or more flame traps, one or more filters, sealing and insulating systems, a dry booster pump or a combination of dry booster pumps, such as for example "Roots" pumps;

the finishing column is fluidically connected to a dry vacuum pump condensation system, at the top of the column, or at the top of the column and laterally to the column;
the dry vacuum pump condensation system is fluidically connected to the finishing column in order to condense a stream distilled at the top of the finishing column, or in order to condense a stream drawn off laterally from the finishing column, or a mixture of these two streams.

Another subject of the invention is a process for producing (meth)acrylic acid comprising at least the following steps:
A) at least one (meth)acrylic acid precursor is subjected to gas-phase oxidation in order to form a gaseous reaction mixture comprising (meth)acrylic acid;
B) the gaseous reaction mixture is cooled;
C) the cooled gaseous reaction mixture is subjected to the process for recovering (meth)acrylic acid as defined above.

The present invention makes it possible to overcome the drawbacks of the prior art linked to the use of a solvent-free recovery/purification process that requires a purified (meth)acrylic acid to be obtained.

DESCRIPTION OF THE DRAWINGS

Other characteristics and advantages of the invention will more clearly emerge on reading the detailed description which follows, with reference to the appended FIGS. 1 to 4, which represent.

DETAILED DESCRIPTION OF THE INVENTION

The invention is based on the incorporation of a dry vacuum pump fluidically connected to a condenser that forms a dry vacuum pump condensation system in a process for producing (meth)acrylic acid.

Figure 1:
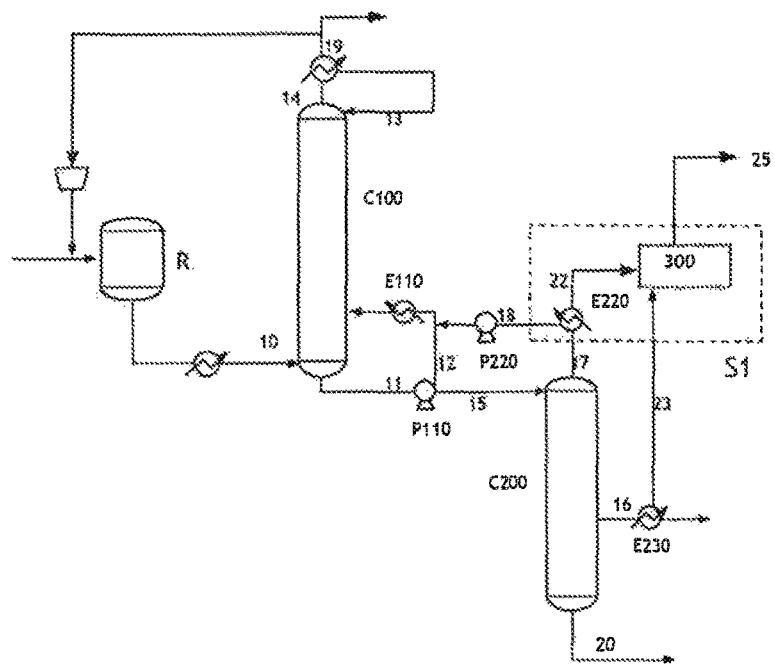
FIG. 1: diagram of a process for producing acrylic acid that illustrates the solvent-free recovery/purification process according to the invention.

Seen in FIG. 1 is a reactor R that produces a gaseous reaction mixture 10 comprising (meth)acrylic acid obtained by gas-phase oxidation of a (meth)acrylic acid precursor. The gaseous reaction mixture comprising a water/(meth)acrylic acid weight ratio generally of between 0.3 and 2 may be precooled before being subjected to a dehydration according to step i) of the process according to the invention in a first column C100 referred to as a dehydration column. The dehydration column results in an overhead stream 14, of which one portion is condensed and sent back to the dehydration column in the form of reflux 13 in order to absorb the (meth)acrylic acid, the other portion 19 comprising the noncondensable light compounds generally being sent partially or completely to a purification device or partly recycled to other steps of the (meth)acrylic acid production process, preferably to a step located upstream of the reactor R.

According to one embodiment, the reactor R is a set of two reactors in series or comprises at least two reaction zones in series, the first reactor or the first reaction zone being used for the synthesis of the (meth)acrylic acid precursor.

According to one embodiment, the whole of the overhead stream 14 from the dehydration column is sent to the overhead condenser.

The objective of step i) is to eliminate, in an overhead stream, most of the water present in the reaction mixture, but also the noncondensable light compounds and the condensable light compounds. The dehydration column operates, at least partially, as a distillation column. It is fed in its lower part by the reaction mixture 10. It generates an overhead stream 14 comprising most of the water and light compounds, this overhead stream being depleted in (meth) acrylic acid, and a bottom stream 11 comprising most of the (meth)acrylic acid with heavy by-products.

Advantageously, the dehydration column operates at atmospheric pressure or slightly above atmospheric pressure, up to $1.5 \times 10^5$ Pa.

Advantageously, the temperature in the upper part of the dehydration column is at least 40° C., preferably is between 40° C. and 80° C. The temperature of the bottom stream from the dehydration column preferably does not exceed 120° C.

According to the invention, most of the water present in the gaseous reaction mixture comprising (meth)acrylic acid is eliminated during step i) without there being excessive loss of acrylic acid in the overhead stream 19.

No azeotropic solvent is added to the dehydration column.

The weight content of water in the bottom stream from the dehydration column is generally less than 10%, preferably less than 7%.

According to step ii) of the process according to the invention, the bottom stream 11 from the dehydration column is sent, at least in part (stream 15), to the top of a second distillation column referred to as a finishing column, or purification column, C200, in which an overhead stream 17 and a bottom stream 20 are separated.

Alternatively, the bottom stream from the dehydration column is sent, at least in part, between the top and the sidestream from the purification column.

The bottom stream from the dehydration column may pass, in part, into an intermediate tank before entering the purification column.

According to one embodiment, a portion 12 of the bottom liquid stream 11 from the dehydration column is sent via a pump P110 to a heat exchanger E110, which may be a heater or a cooler and is reinjected into the dehydration column, so as to form a bottom loop. Preferably, the portion 12 of the bottom stream is reinjected between the feed of the gaseous reaction mixture and the top of the dehydration column. The remainder (stream 15) of the liquid stream 11 is sent by the same pump P110 as feed for the finishing (or purification) column C200.

The dehydration column and the finishing column may have various configurations, for example of the type of a column with random or structured packing or a plate column.

The dehydration column generally comprises from 5 to 50 theoretical plates, preferably from 20 to 30 theoretical plates; the finishing column generally comprises from 5 to 30 theoretical plates, preferably from 8 to 20 theoretical plates. The choice of the type of internals in the columns and the choice of the additional equipment such as heat exchangers, condensers, pumps, fluid inlets and outlets will be easily determined according to the considerations known to person skilled in the art.

The finishing (or purification) column is a distillation column associated with a reboiler and a condenser.

The temperature and the pressure in the purification column are not critical, and may be determined in accordance with the distillation methods known in the prior art. However, preferably, the purification column operates at a pressure below atmospheric pressure, making it possible to operate at relatively low temperatures, thus preventing the polymerization of the unsaturated products present, and minimizing the formation of heavy by-products.

Advantageously, the purification column operates under a pressure ranging from 5 kPa to around 60 kPa, the temperature of the overhead stream advantageously being between 410° C. and around 90° C., and the temperature of the bottom stream being between 60° C. and 120° C.

According to the recovery process of the invention, the overhead gaseous stream 17 from the finishing column C200 is sent, at least in part, preferably entirely, to a dry vacuum pump condensation system S1, represented in FIG. 1 by the assembly consisting of the condenser E220 and the dry vacuum pump 300. The condensed liquid 18 mainly containing light compounds, in particular water and acetic acid, and also (meth)acrylic acid, is advantageously recycled via a pump P220 to the dehydration column C100. The uncondensed effluent 22 at the outlet of the condenser E220 is introduced into the dry pump 300, before being eliminated in the form of a final gaseous effluent 25.

The use of such a system S1 incorporating a dry vacuum pump provides a pressure below atmospheric pressure in the finishing column, thus making it possible to eliminate, at reduced temperature, the residual light compounds resulting from the prior step of dehydration of the reaction mixture comprising the (meth)acrylic acid.

No aqueous effluent is produced by the dry vacuum pump condensation system.

Examples of dry piston-type vacuum pumps are described for example in document US 2005/260085 or U.S. Pat. No. 5,921,755. The dry vacuum pumps may also be composed, for example, of a cylindrical body in which a rotor in an off-centre position rotates, provided with notches inserted into which are vanes that make it possible to suck up a gaseous stream. Any other type of configuration may be used as a dry vacuum pump. The term "dry" indicates that no liquid stream, such as a lubricating oil or water, is in contact with the gaseous stream supplying the pump.

As examples of dry vacuum pumps, mention may be made, without this list being limiting, of dry screw mechanical pumps, bellows seal pumps, scroll pumps, rotary piston pumps, rotary lobe pumps, oil-free diaphragm membrane pumps, for example the dry screw vacuum pumps sold by Edwards, or the rotor-type pumps sold by Sihi. These pumps create a primary vacuum which may, if necessary, be supplemented by other dry vacuum pumps, such as for example booster dry pumps of "Roots" type.

Advantageously, the vacuum obtained in the finishing column may be adjusted as a function of the operating speed of the dry vacuum pump.

A (meth)acrylic acid stream 16 is recovered by drawing off as a sidestream from the finishing column (step iii), at a lateral level preferably located below the feed of said column. The product stream 16 drawn off may be a liquid stream or gaseous stream.

The stream 16 drawn off as a sidestream corresponds to a technical grade of (meth)acrylic acid. In general, it consists of (meth)acrylic acid having a purity of greater than 98%, preferably greater than 99%. Preferably, it contains less than 1.5%, preferably less than 0.5%, more particularly less than 0.2% by weight of acetic acid, and less than 1%, preferably less than 0.5%, more particularly less than 0.3% by weight of water. The stream 16 may also be subjected to a purification by distillation, optionally coupled with a crystallization treatment.

According to one preferred embodiment of the invention, at least one portion of the purified (meth)acrylic acid stream 16 drawn off as a sidestream is subjected to a dry vacuum pump condensation system which may comprise the dry vacuum pump 300 used at the top of the finishing column.

According to an embodiment, the stream 16 is subjected to a condensation in a condenser E230 and the gaseous stream 23 is sent to the vacuum pump 300.

Figure 2:
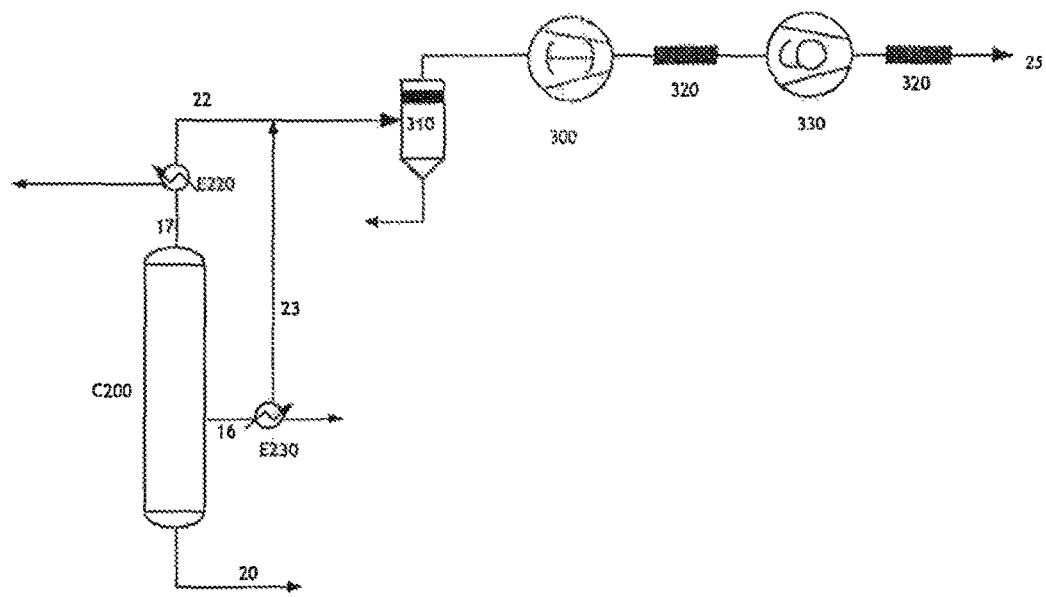
FIG. 2: plant suitable for the implementation of the recovery process illustrating an embodiment of the invention.

According to one particular embodiment of the invention, as represented in FIG. 2, the gaseous stream 22, optionally mixed with the stream 23, supplying the dry vacuum pump, first passes into a liquid separator device 310, which makes it possible to separate the traces of residual liquid, rich in light compounds, in particular water and acetic acid, and also residual (meth)acrylic acid. Preferably, this liquid stream will be recycled to the dehydration column, for example as a mixture with the stream 18 supplying the pump P220.

According to other embodiments, the gas 25 at the outlet of the dry vacuum pump passes through various components, such as those described above, in particular at least one flame trap 320, and a dry booster pump 330, before being sent finally to an incinerator.

The condensate 18, formed by the dry vacuum pump condensation system, is advantageously sent back, partially or completely, to the dehydration column, between the bottom and the top of the column and preferably above the feed of the gaseous reaction mixture. According to one embodiment, it is mixed with the stream 12 from the bottom loop of the dehydration column, as represented in FIG. 1.

Optionally, the stream 18 may pass into an intermediate storage tank before recycling to the bottom loop of the dehydration column.

A (meth)acrylic acid stream 20 comprising most of the heavy by-products, especially Michael addition products and also polymerization inhibitors, is recovered at the bottom of the finishing column (step iii).

The bottom stream 20 from the finishing column corresponds to a crude (meth)acrylic acid grade that may be used directly as raw material in a unit for producing acrylic esters by direct esterification, or optionally after a step of thermal decomposition of the Michael addition derivatives releasing (meth)acrylic acid. Alternatively, the bottom stream 20 may be purified in a third distillation column in order to obtain a technical grade (meth)acrylic acid.

Advantageously, the product stream 16 drawn off as a sidestream and the bottom stream 20 from the finishing column are recovered in a weight ratio ranging from 99:1 to 25:75, preferably from 98:2 to 50:50.

Polymerization inhibitors may be introduced at various locations in the plant for implementing the process of the invention, especially into the overhead stream from the dehydration column level with the condenser, or into the overhead stream from the purification column level with the condenser associated with said column, or into the purified product stream drawn off as a sidestream from the purification column, optionally after condensation in the case where the stream drawn off is in gaseous form.

The polymerization inhibitors are selected from the compounds that inhibit the polymerization reaction of (meth) acrylic acid and are added in an amount known to a person skilled in the art that is sufficient to prevent or reduce the polymerization of (meth)acrylic acid. As examples of compounds that can be used, mention may be made of phenothiazine, hydroquinone, 2,2,6,6-tetramethyl-1-piperidinyloxy (TEMPO) or a derivative thereof such as 4-hydroxy TEMPO, soluble copper salts, soluble manganese salts, alone or as a mixture, optionally in solution in water, in (meth)acrylic acid or in a mixture of water and (meth)acrylic acid.

According to one embodiment of the invention, the nature of the inhibitor varies depending on the location where it is injected.

According to one embodiment of the invention, air or an oxygen-containing gas is introduced, for example into the bottoms of the dehydration and purification columns, into the reboilers of the columns, into the recirculation loop at the bottom of the dehydration column or level with the sidestream from the purification column or into the condensers.

The process of the invention directly provides, as sidestream from the finishing column, a (meth)acrylic acid quality that corresponds to a technical grade (meth)acrylic acid, which may be then sent to a purification unit, for example unit for purification by crystallization, in order to obtain a "glacial" (meth)acrylic acid quality. It also provides, at the bottom of the finishing column, a crude (meth) acrylic acid quality that may then be purified or treated thermally in order to obtain a technical grade (meth)acrylic acid.

The plant according to the invention suitable for implementing the process for recovering/purifying (meth)acrylic acid as described, comprises at least:

a) one dehydration column C100;
b) one finishing column C200 fluidically connected to the bottom of said dehydration column;
c) at least one E220/300 dry vacuum pump condensation system S1, fluidically connected to the top of said finishing column;
d) optionally one E230/300 dry vacuum pump condensation system fluidically, connected laterally to said finishing column.

Another subject of the invention relates to a process for producing (meth)acrylic acid comprising at least the following steps:

A) at least one (meth)acrylic acid precursor is subjected to gas-phase oxidation in order to form a gaseous reaction mixture comprising (meth)acrylic acid;
B) the gaseous reaction mixture is cooled;
C) the cooled gaseous reaction mixture is subjected to the process for recovering (meth)acrylic acid as defined above.

The (meth)acrylic acid precursor may be acrolein or methacrolein, and may be derived from renewable raw material thus producing biobased (meth)acrylic acid.

Preferably, the (meth)acrylic acid is acrylic acid and the acrylic acid precursor is acrolein obtained by catalytic oxidation of propylene.

The oxidation reaction of step A), carried out according to the knowledge of the art, generally provides a gaseous reaction mixture, superheated to a temperature above 280° C.

This mixture is advantageously cooled according to a step B), in particular down to a temperature below 250° C., preferably below 190° C., in order to be subjected, according to step C), to the process for recovering the (meth)acrylic acid without using an azeotropic solvent and including a dry vacuum pump condensation system. It may be cooled directly in the dehydration column, or may be cooled using a heat exchanger located upstream of the dehydration column.

Even though the use of the dry vacuum pump condensation system is described in the present invention in a process for producing (meth)acrylic acid including a solvent-free purification process with two distillation columns, the dry vacuum pump condensation system may also be used in other processes that produce a gaseous reaction mixture, in order to reduce the amount of water and vapour used, and to thus reduce the amount of aqueous effluents discharged.

The invention will now be illustrated by the following examples, the objective of which is not to limit the scope of the invention defined by the appended claims.

EXPERIMENTAL SECTION

Example 1 (According to the Invention)

Simulations using ASPEN software have been used to illustrate the process according to the invention.

With reference to FIG. 1, in a process for the continuous production of acrylic acid from propylene, a reaction mixture 10 was subjected to the recovery/purification process according to the invention.

In this process, 11 000 kg/h of technical acrylic acid are produced (stream 16), having a purity of 99.8%. The main impurities are acetic acid (0.05%), propionic acid (0.021%), furfural (0.014%), benzaldehyde (0.008%) and maleic anhydride (0.037%).

The gaseous stream 22 (67.6 kg/h) originating from the condenser E220 at the top of the finishing column C200 was subjected to a dry vacuum pump 300. This pump provides a pressure of 12 kPa at the top of the column C200. A stream 23 (7.3 kg/h) originating from the condenser E230 placed at the side outlet of the technical acrylic acid stream was sent at the same time to the dry vacuum pump 300.

The main constituents of the incoming streams 22 and 23, and also the composition of the outgoing gaseous stream 25 expressed as hourly mass flow rate (kg/h), are given in Table 1.

No aqueous effluent is produced according to this system.

At the outlet of the dry vacuum pump, only a final gaseous effluent 25 (74.9 kg/h) is limited, which is easy to eliminate by methods known to person skilled in the art, for example by thermal or catalytic oxidation.

The loss of acrylic acid in the stream 19 cooled to 57° C. is 0.69%, i.e. an acrylic acid recovery yield of 99.31%.

TABLE 1

| Mass flow rate kg/h | Stream 22 | Stream 23 | Gaseous effluent stream 25 |
|---|---|---|---|
| $N_2$ | 4.823E+00 | 0.000E+00 | 4.823E+00 |
| $O_2$ | 3.032E+01 | 6.134E+00 | 3.646E+01 |
| CO | 2.441E−02 | 0.000E+00 | 2.441E−02 |
| $CO_2$ | 1.431E−01 | 0.000E+00 | 1.431E−01 |
| Propylene | 6.118E−01 | 0.000E+00 | 6.118E−01 |
| Propane | 1.990E−01 | 0.000E+00 | 1.990E−01 |
| Formaldehyde | 7.109E−01 | 0.000E+00 | 7.109E−01 |
| Acetaldehyde | 6.608E−03 | 0.000E+00 | 6.608E−03 |
| Acrolein | 3.537E−01 | 0.000E+00 | 3.537E−01 |
| $H_2O$ | 8.108E+00 | 2.316E−09 | 8.108E+00 |
| Acetic acid | 4.870E+00 | 1.441E−03 | 4.871E+00 |
| Acrylic acid | 1.739E+01 | 1.181E+00 | 1.857E+01 |
| Propionic acid | 1.941E−03 | 2.357E−04 | 2.177E−03 |
| Furfural | 6.446E−04 | 9.564E−05 | 7.402E−04 |
| Benzaldehyde | 4.463E−04 | 3.563E−05 | 4.820E−04 |
| Maleic anhydride | 5.412E−04 | 7.153E−05 | 6.127E−04 |
| TOTAL | 67.571 | 7.316 | 74.887 |

Examples 2 and 3 (Comparative)

Figure 3:
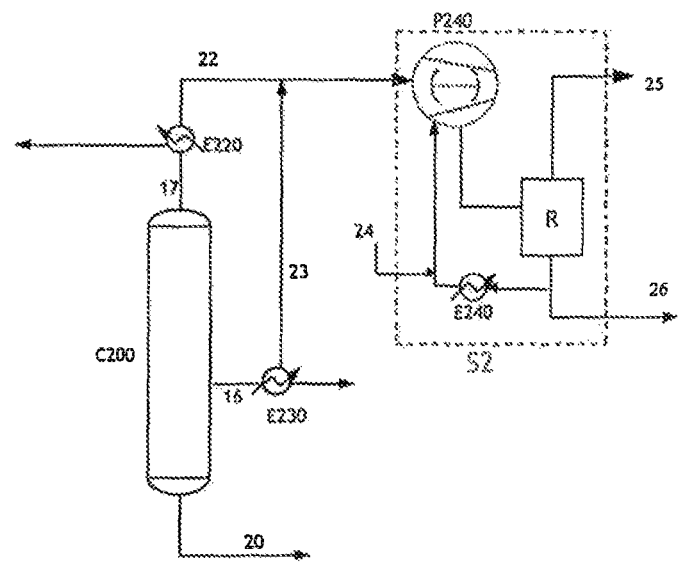
FIG. 3: plant from the prior art that includes a liquid ring pump condensation system.
Figure 4:
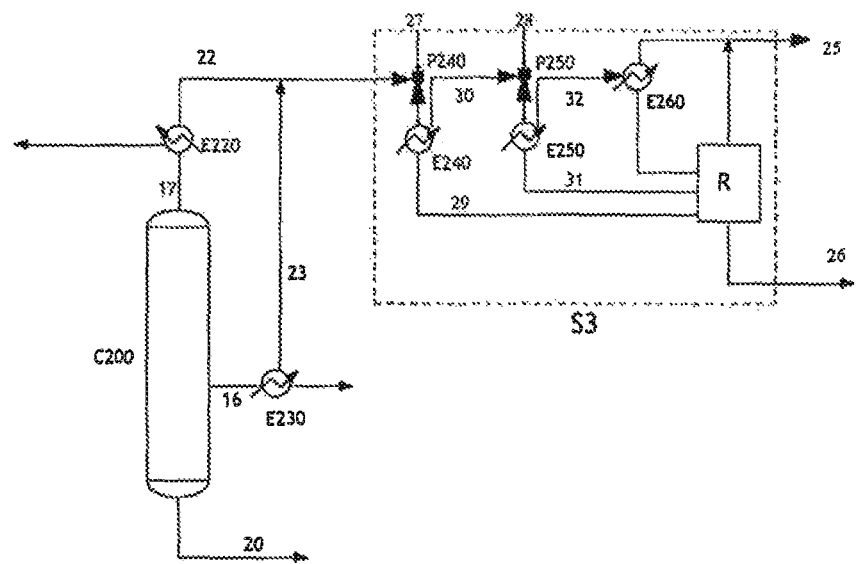
FIG. 4: plant from the prior art with a condensation system that incorporates steam ejectors.

By way of comparison, the same streams 22 and 23 were subjected respectively to a liquid ring pump (Example 2, FIG. 3) as a replacement for the dry vacuum pump, and to a system incorporating steam ejectors (Example 3, FIG. 4).

In particular, Example 3 involves a steam ejector vacuum generator technology described in document U.S. Pat. No. 6,677,482 or 7,288,169.

Represented in FIG. 3 is a system S2 that incorporates a liquid ring pump P240, fed by a water stream 24. The flow rate of the stream 24 introduced into the pump in order to provide a pressure of 12 kPa is 1000 kg/h. This system S2 comprises a pump P240, an exchanger E240 and a receptacle for collecting the condensates R.

The pump P240 is fed on the one hand by the gaseous streams 22 and 23 originating from the column C200 and on the other hand by the aqueous stream 27. The main role of this aqueous stream is to constitute a liquid seal necessary for the generation of the vacuum in the pump and to ensure the replacement of the liquid by purging it of the condenser impurities. The heat released by the pump is eliminated owing to the cooling of the condenser stream through the exchanger.

The stream exiting the pump is partly liquid and partly gaseous. The two phases are separated in the receptacle R and a portion of the (essentially aqueous) liquid phase is recirculated to the pump P240 after cooling in the exchanger E240.

This system S2 therefore produces, at the outlet, a gaseous stream 25 (43.2 kg/h), but also a liquid effluent 26 in a large amount (1031.7 kg/h). This essentially aqueous stream 26 contains organic compounds in solution, at high concentrations (mainly 1.8% acrylic acid, 0.5% acetic acid), which make it unsuitable for discharging without supplementary purification treatment.

Represented in FIG. 4 is a system S3 that incorporates two ejectors in series P240 and P250, fed respectively by 400 kg/h of steam (stream 27) and 600 kg/h of steam (stream 28), so as to ensure a pressure of 12 kPa at the top of the column C200.

This system S3 comprises the two pumps (ejectors) mounted in series which are fed by steam at a pressure of 1500 kPa and three condensers.

The first ejector P240 is fed on the one hand by the gaseous streams 22 and 23 originating from the column C200 and on the other hand by the pressurized steam stream. The outgoing gaseous stream at a temperature of 144° C. is cooled to a temperature of 42° C. in a first condenser E240. The liquid condensate 29 is sent to a receptacle for collecting the condensates R and the uncondensed gaseous effluents 30 are sent to the feed of the second ejector P250. On leaving this ejector, the gaseous stream at 162° C. is cooled to a temperature of 42° C. in the condenser E250. The condensed liquid stream 31 is sent to the receptacle R. The effluents 32 not condensed in this second condenser are cooled to 15° C. in the third condenser E260, producing a third liquid condensate recovered in the reservoir R. The gaseous stream 25 not condensed in this third condenser is eliminated.

This system S3 thus produces, at the outlet, a gaseous stream 25 (42.8 kg/h), but also an aqueous effluent 26 in a large amount (1032.1 kg/h). This aqueous stream 26 contains organic compounds in solution, at high concentrations (mainly 1.8% acrylic acid, 0.5% acetic acid), which make it unsuitable for discharging without supplementary purification treatment.

The main constituents of the gaseous stream 25 and of the aqueous stream 26 at the outlet of the systems S2 and S3 are indicated in Table 2.

TABLE 2

| Mass flow rate kg/h | Example 1 Gaseous stream 25 | Example 2 (comp) Gaseous stream 25 | Example 2 (comp) Aqueous stream 26 | Example 3 (comp) Gaseous stream 25 | Example 3 (comp) Aqueous stream 26 |
|---|---|---|---|---|---|
| $N_2$ | 4.823E+00 | 4.820E+00 | 2.845E−03 | 4.821E+00 | 1.453E−03 |
| $O_2$ | 3.646E+01 | 3.642E+01 | 3.737E−02 | 3.644E+01 | 1.931E−02 |
| CO | 2.441E−02 | 2.439E−02 | 1.782E−05 | 2.439E−02 | 1.207E−05 |
| $CO_2$ | 1.431E−01 | 1.376E−01 | 5.575E−03 | 1.410E−01 | 2.102E−03 |
| Propylene | 6.118E−01 | 6.076E−01 | 4.248E−03 | 6.107E−01 | 1.148E−03 |
| Propane | 1.990E−01 | 1.987E−01 | 2.888E−04 | 1.989E−01 | 1.124E−04 |
| Formaldehyde | 7.109E−01 | 9.219E−04 | 7.099E−01 | 5.115E−05 | 7.108E−01 |
| Acetaldehyde | 6.608E−03 | 8.909E−04 | 5.717E−03 | 1.830E−03 | 4.778E−03 |
| Acrolein | 3.537E−01 | 9.535E−02 | 2.584E−01 | 1.591E−01 | 1.946E−01 |
| $H_2O$ | 8.108E+00 | 8.758E−01 | 1.007E+03 | 4.162E−01 | 1.008E+03 |
| Acetic acid | 4.871E+00 | 2.005E−03 | 4.869E+00 | 1.634E−05 | 4.871E+00 |
| Acrylic acid | 1.857E+01 | 7.855E−03 | 1.857E+01 | 6.686E−05 | 1.857E+01 |
| Propionic acid | 2.177E−03 | 1.239E−06 | 2.175E−03 | 1.878E−08 | 2.177E−03 |
| Furfural | 7.402E−04 | 4.273E−06 | 7.360E−04 | 2.027E−06 | 7.382E−04 |
| Benzaldehyde | 4.820E−04 | 3.393E−05 | 4.480E−04 | 5.944E−05 | 4 225E−04 |
| Maleic anhydride | 6.127E−04 | 5.197E−08 | 6.127E−04 | 2.376E−11 | 6.127E−04 |
| TOTAL | 74.887 | 43.191 | 1031.697 | 42.811 | 1032.075 |

The conventional vacuum systems involving a liquid ring pump, or steam jet ejectors generate a large amount of aqueous effluent. This effluent contains organic impurities and must therefore be treated.

Example 4

In order to avoid the expensive treatment of the aqueous stream resulting from the liquid ring pump (Example 2) or from the ejector system (Example 3), and to recover a portion of the acrylic acid contained in these streams, it may be envisaged to recycle these streams to the solvent-free purification process.

A simulation of the solvent-free purification process was carried out using ASPEN software, incorporating a recycling of the aqueous stream 26 condensed in Example 3 (ejectors in series), as a mixture with the stream 18 sent to the dehydration column C100 (see FIG. 1).

Under these conditions, contrary to the desired objective, it is observed that the recycling of this aqueous stream (1032 kg/h) gives rise to a significant loss of acrylic acid at the top of the condensation column C100.

The loss of acrylic acid in the stream 19 cooled to 61° C. is 1.74%, i.e. an acrylic acid recovery yield of 98.26%.

The invention claimed is:

1. A process for recovering (meth)acrylic acid without using azeotropic solvent, starting from a gaseous reaction mixture comprising (meth)acrylic acid obtained by gas-phase oxidation of a precursor of the (meth)acrylic acid, comprising at least the following steps:
   i) subjecting the gaseous reaction mixture to dehydration without using azeotropic solvent in a dehydration column, resulting in a dehydration column overhead stream, at least a portion of which is condensed and sent back to the dehydration column in the form of reflux, and in a dehydration column bottom stream;
   ii) subjecting the dehydration column bottom stream, at least in part, to a distillation at a pressure below atmospheric pressure in a finishing column, resulting in a finishing column overhead stream and in a finishing column bottom stream containing heavy compounds;
   iii) recovering a (meth)acrylic acid stream by drawing off as a sidestream from the finishing column, and/or as bottoms from the finishing column;
   subjecting the finishing column overhead gaseous stream, at least in part, to a dry vacuum pump condensation system such that the finishing column operates under vacuum, thereby eliminating or reducing generation of aqueous discharge and forming a condensate comprising light compounds that is recycled back to the dehydration column, and a final gaseous effluent.

2. The process according to claim 1, wherein the dry vacuum pump condensation system comprises at least one condenser and one dry vacuum pump.

3. The process according to claim 1 wherein the dry vacuum pump condensation system additionally comprises a liquid separator, or one or more flame traps, or one or more filters, or sealing and insulating systems, or a dry booster pump or a combination of dry booster pumps.

4. The process according to claim 1 wherein at least one portion of the (meth)acrylic acid stream drawn off as a sidestream is subjected to a dry vacuum pump condensation system, identical to or different from that used for the finishing column overhead stream from the finishing column.

5. The process according to claim 1 wherein the precursor of the (meth)acrylic acid is acrolein, obtained by oxidation of propylene or by oxydehydrogenation of propane.

6. The process according to claim 1 wherein the precursor of the (meth)acrylic acid is methacrolein, obtained by oxidation of isobutylene and/or of tert-butanol or from oxydehydrogenation of butane and/or isobutane.

7. The process according to claim 1 wherein the precursor of the (meth)acrylic acid comprises carbon of renewable origin.

8. The process according to claim 7 wherein the precursor of the (meth)acrylic acid is derived from glycerol, 3-hydroxypropionic acid or 2-hydroxypropanoic acid.

9. The process according to claim 1 further comprising the step of purifying the (meth)acrylic acid stream recovered in step iii).

10. The process for producing (meth)acrylic acid comprising at least the following steps:
   A) subjecting at least one (meth)acrylic acid precursor to gas-phase oxidation to form a gaseous reaction mixture comprising (meth)acrylic acid;
   B) cooling the gaseous reaction mixture;
   C) subjecting the cooled gaseous reaction mixture to the process for recovering (meth)acrylic acid as recited in claim 1.

11. The process according to claim 10, wherein the (meth)acrylic acid is acrylic acid and the acrylic acid precursor is acrolein obtained by catalytic oxidation of propylene.

12. A system for recovering (meth)acrylic acid without using azeotropic solvent according the process of claim 1, comprising at least:
   a) one dehydration column;
   b) one finishing column fluidically connected to the bottom of said dehydration column;
   c) at least one dry vacuum pump condensation system, fluidically connected to the top of said finishing column;

d) optionally one dry vacuum pump condensation system fluidically connected laterally to said finishing column.

\* \* \* \* \*